United States Patent
Ranganathan et al.

(10) Patent No.: US 8,325,048 B2
(45) Date of Patent: Dec. 4, 2012

(54) THERMAL STRESS INDICATOR

(75) Inventors: Sridhar Ranganathan, Suwanee, GA (US); Andrew Thomas Baker, Norcross, GA (US); Jeffrey Heller, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 406 days.

(21) Appl. No.: 12/633,025

(22) Filed: Dec. 8, 2009

(65) Prior Publication Data
US 2011/0133939 A1 Jun. 9, 2011

(51) Int. Cl.
G08B 17/00 (2006.01)
G08B 13/14 (2006.01)
G08B 23/00 (2006.01)
G08B 21/00 (2006.01)
G08C 19/12 (2006.01)

(52) U.S. Cl. ..... 340/584; 340/586; 340/589; 340/572.1; 340/573.1; 340/870.16; 340/870.17

(58) Field of Classification Search ............ 340/584
See application file for complete search history.

(56) References Cited

U.S. PATENT DOCUMENTS

| | | | |
|---|---|---|---|
| 6,257,759 B1 | 7/2001 | Witonsky et al. | |
| 6,292,685 B1 | 9/2001 | Pompei | |
| 7,532,106 B2 * | 5/2009 | Debord et al. | 340/309.16 |
| 7,800,505 B2 * | 9/2010 | Pietersen | 340/573.1 |
| 2006/0122473 A1 | 6/2006 | Kill et al. | |
| 2006/0290496 A1 | 12/2006 | Peeters | |
| 2007/0027403 A1 | 2/2007 | Kosted | |
| 2007/0282218 A1 | 12/2007 | Yarden | |
| 2007/0295713 A1 * | 12/2007 | Carlton-Foss | 219/497 |
| 2008/0146871 A1 | 6/2008 | Arneson et al. | |
| 2008/0262320 A1 | 10/2008 | Schaefer et al. | |
| 2009/0188017 A1 * | 7/2009 | Kruse | 2/81 |
| 2010/0054300 A1 * | 3/2010 | Tsai | 374/141 |
| 2010/0321190 A1 * | 12/2010 | Montague | 340/584 |

FOREIGN PATENT DOCUMENTS

| | | |
|---|---|---|
| WO | WO 2008/006150 A1 | 1/2008 |
| WO | WO 2008/035151 A2 | 3/2008 |
| WO | WO 2008/095183 A2 | 8/2008 |

* cited by examiner

*Primary Examiner* — Jennifer Mehmood
*Assistant Examiner* — John Mortell
(74) *Attorney, Agent, or Firm* — Nancy M. Klembus; Ralph H. Dean

(57) ABSTRACT

The present invention provides a device for non-invasive monitoring thermal stress of a user. The device is capable of monitoring the internal body temperature and changes in the internal body temperature of a user. Also, the device is capable of alerting a user when the user is in danger of thermal stress.

19 Claims, 8 Drawing Sheets

THERMAL STRESS INDICATOR

FIELD OF THE INVENTION

The present invention generally relates to a thermal stress indicator and the method of using the thermal stress indicator.

BACKGROUND

Under normal circumstances the human body is exceptionally efficient at regulating a constant internal temperature. However, increased workload compounded by environmental factors such as air temperature, radiant heat sources, and humidity may stress the body's ability to safely regulate its internal temperature. Heat stress is a potentially dangerous build up of heat within a body and is a hazard faced by many workers and athletes. The use of necessary protective apparel when working in hot environments puts such workers at an increased risk of heat stress. On the other end of the temperature spectrum, workers in cold environments are at risk of an unsafe decrease in the body core temperature known as hypothermia.

The current industry practice to limit the potential hazard of thermal stress includes controlling work/rest cycles based on environmental conditions. Such guidelines are conservative estimates based on average workers and vary based on a person's age, weight, physical fitness, degree of acclimation, use of alcohol or drugs, various medical conditions, clothing being worn, and other individual-specific factors. Thermal stress, including both heat stress and hypothermia, is indicated by several physiological changes and has been studied extensively in the past. Many thermal stress indicators involve consideration of the environmental factors and individual-specific factors as discussed above and comparing them with known tabulated data. However, such measurements and use of reference materials is not necessarily convenient or practical in the average dynamic work environment.

One key indicator for determining the onset of thermal stress (either heat stress or hypothermia) is the true core body temperature. Multiple safety standards agree that the body core temperature should not be allowed to exceed 38° C. for extended periods of time, nor should the core temperature be allowed to increase at a rate of much greater than 1° C. per hour. Similarly, the onset of hypothermia occurs when the body core temperature drops below 35° C. Having a core body temperature outside the range of about 35° C. to about 38° C. can result in the failure of various systems of the body and may ultimately result in death.

There are several known methods to measure/estimate core temperature. Invasive techniques used include rectal probes, esophageal catheters or capsules that are swallowed. When patients are catheterized, blood temperature or urine temperature in the bladder may also be used as a good indicator of core body temperature. While such invasive measurement methods work well for patients in a controlled environment, such techniques are not feasible for use with workers in a comparatively uncontrolled working environment or for an athlete undertaking their particular activity. Such invasive methods are even less practical in situations where continuous monitoring the core temperature of such a worker or athlete is desired.

Several minimally invasive methods of estimating the core body temperature from skin temperature measurements have been developed. Due to the differences between the skin temperature and the core body temperature, such methods have to modify the measured skin temperature to estimate the true body core temperature. Some estimates modify the measured skin temperature utilizing other environmental data such as ambient temperature and ambient humidity, either measured by the device or inputted by the user. Other estimates of core body temperature require input or acquisition of user-specific data. For example, a series of baseline measurements may be taken over a period of time to calibrate the skin temperature measurements for the particular user. Other estimates are left in insulated contact with the skin of the user until a presumed equilibrium of body core temperature and skin temperature is reached in the region of insulated contact. All of such estimates of body core temperature are often adequate for monitoring the temperature of a patient in the controlled care environment.

However, such estimates of core temperature are user-specific and are not practical for the working environs, and under the conditions, in which a worker or athlete may be at risk for thermal stress and would particularly benefit from such monitoring. For example, as a worker (or athlete) exerts himself or herself, their body temperature may rapidly increase. Their body will attempt to regulate the internal body temperature through various methods including increasing perspiration for the purposes of evaporative cooling. In such situations of rapid temperature change and cooling of the skin by perspiration, the assumptions underlying existing models of estimating core temperature from skin temperature are broken. Thus, estimates of core body temperature may become more inaccurate in situations of rapid temperature change and increased subject perspiration; the very situations in which such thermal stress monitoring is most needed.

SUMMARY OF THE INVENTION

Generally stated, the present invention provides a device for non-invasive monitoring thermal stress of a user. The device is capable of monitoring the internal body temperature and changes in the internal body temperature of a user. Also, the device is capable of alerting a user when the user is in danger of thermal stress.

The device has a monitoring unit which has a first substrate and at least two temperature sensors. This first substrate has a first side and an opposite second side. The at least two temperature sensors which are located on the substrate, wherein at least one temperature sensor is located on the first side of the first substrate and at least one temperature sensor is located on the second side of the first substrate. Each temperature sensor is directly or indirectly connected to the first substrate. The device further has a cover and this cover has cover comprising a first side and an opposite second side. The first side of the cover has a defined surface area, wherein this defined surface area has a first area and a second area. The cover is adapted to receive monitoring unit in the first area of said defined area.

In one embodiment, the monitoring device has an adhesive applied to a portion of the second area of the cover. The adhesive is a way to hold the monitoring device against the skin of a user during use. The adhesive may be a pressure sensitive adhesive adapted to be applied to the skin of a user. The pressure sensitive adhesive may be advantageously be covered with a release sheet to protect the pressure sensitive adhesive prior to use.

In another embodiment, the device may be constructed such that the first substrate is a circuit board.

In a further embodiment, the device further has a shell directly or indirectly connected to the first substrate wherein the shell essentially covers the second side of said first substrate of the monitoring unit.

The device may also have a thermally conductive member which contacts the temperature sensor on the second side of the first substrate. The thermally conductive member extends through the second side of the cover and is exposed to the environment outside of the monitoring device.

To alert the user or others around the user of a potential thermal stress situation, the device, in an embodiment, may have an alert mechanism. The alert mechanism may be an audible alarm, a visual alarm, a tactile alarm, an action to provide heating or cooling to the user, or a combination thereof.

The device may have additional features including a processor attached to the first substrate. The processor is configured to receive input from each temperature sensor and is configured to determine a core temperature of the user of the device. Generally, the processor is configured to compare the determined core temperature to stored threshold core temperature value and if the determined core temperature is outside the threshold core temperature value to output an alert signal. Alternatively or in conjunction with the determination of the core temperature, the processor may be configured to compare the measured rate of change in core temperature to a stored threshold rate of change in core temperature range and is configured to output an alert signal when the determined rate of change in core temperature is outside the stored threshold rate of change in core temperature.

In a further embodiment, the cover of the device may be prepared from a flexible material.

The device of the present invention maybe disposable or reusable. In one embodiment, the cover is removable from the monitoring unit and the cover is disposable, while the monitoring unit is reusable.

In one particular embodiment of the present invention, the device for non-invasive monitoring thermal stress of a user has a monitoring unit. The monitoring unit has first substrate having a first side and an opposite second side. There are at least two temperature sensors, wherein at least one temperature sensor is located of the first side of the first substrate and at least one temperature sensor is located on the second side of the first substrate. Each temperature sensor is directly or indirectly connected to said first substrate. A shell is directly or indirectly connected to the first substrate, and the shell essentially covers the second side of said first substrate. The device further has a thermally conductive member, and this thermally conductive member contacts the temperature sensor on the second side of the first substrate and extends through the shell.

In one particular embodiment, the device for non-invasive monitoring of thermal stress of a user has a monitoring unit and a cover. The monitoring unit contains a first substrate comprising a first side and an opposite second side; at least two temperature sensors; a processor; an alert mechanism; and a power supply. At least one temperature sensor is located of the first side of the first substrate and at least one temperature sensor is located on the second side of the first substrate. Each temperature sensor is directly or indirectly connected to the first substrate and each temperature sensor is connected to the processor. The processor is configured receive temperature readings from each temperature sensor to determine a core temperature of the user. The processor also may be configured to determine a rate of change in the core temperature of the user. Further, the processor is configured to compare the determined core temperature to stored threshold core temperature value and if the determined core temperature is outside the threshold core temperature value to output an alert signal. Alternatively or in conjunction with the determination of the core temperature, the processor may be configured to compare the measured rate of change in core temperature to a stored threshold rate of change in core temperature range and is configured to output an alert signal when the determined rate of change in core temperature is outside the stored threshold rate of change in core temperature. The alert mechanism is connected to the processor and is configured to alarm the user when the processor outputs the alert signal. The power supply being connected to the processor and the power supply is configured to provide power to the processor and alert mechanism. The cover has a first side and an opposite second side, where the first side of said cover has a defined surface area. This defined surface area has a first area and a second area and the cover being adapted to receive monitoring unit in the first area of said defined surface area.

The present invention further provides a method of monitoring thermal stress in a user. This method includes providing a monitoring unit, providing a cover, placing the monitoring unit into the cover and applying the monitoring unit and cover combination onto the skin of a user. The monitoring unit has a first substrate, the first substrate having a first side and an opposite second side and at least two temperature sensors. At least one temperature sensor is located of the first side of the first substrate and at least one temperature sensor is located on the second side of the first substrate, and each temperature sensor is connected to the first substrate. The cover has a first side and an opposite second side, where the first side of the cover has a defined surface area, the defined surface area has a first area and a second area. The cover is adapted to receive the monitoring unit such that the monitoring unit directly or indirectly contacts the first area of the defined area of the cover. An adhesive is applied to a portion of the second area of the cover.

In one embodiment of the method of the present invention, the monitoring unit/cover combination is applied to the skin of the user in a temporal artery region of the skin of the user.

By providing the thermal stress monitoring device of the present invention, an effective device to monitor and warn a user of the possibility of thermal stress is about to occur or could occur is provided.

DEFINITIONS

Figure 1:
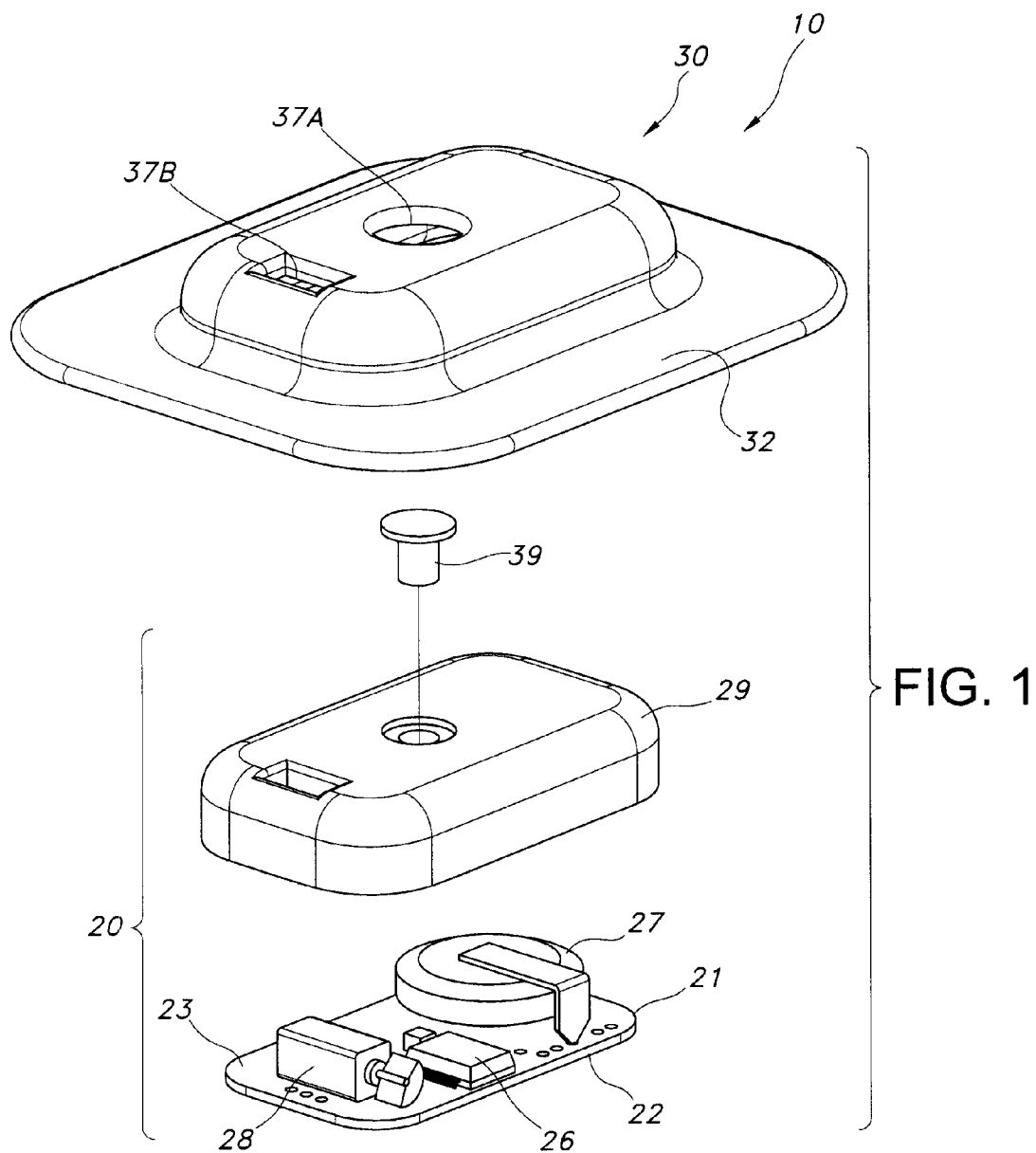
FIG. 1 shows an exploded view of an exemplary thermal stress monitor device within the scope of the present invention.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, the term "thermal stress" refers to a state in which the internal core temperature of a body is outside of the safe operating temperature range. Thermal stress includes states of excessive internal core temperature (i.e., hyperthermia or heat stress) and states of unsafe reduced internal core temperature (i.e., hypothermia).

As used herein, the term "non-invasive" refers to not entering the skin or a body cavity. Non-invasive monitoring involves monitoring that does not include entering the skin, insertion into a body orifice (e.g., insertion into ear, rectum, or other orifice), or otherwise entering a body cavity (e.g., such as by ingestion). "Entering the skin" as used herein, refers to penetrating the skin to a deep enough level to leave a wound or other damage, i.e., typically referring to penetration deeper than the stratum corneum level of the skin.

As used herein, the term "disposable" is not limited to single use articles but also refers to articles that are so relatively inexpensive to the consumer that they can be discarded if they become soiled or otherwise unusable after only one or a few uses.

As used herein, the term "couple" or "affix" includes, but is not limited to, joining, connecting, fastening, linking, or associating two things integrally or interstitially together. As used herein, the term "releaseably affix(ed)" refers to two or more things that are stably coupled together and are at the same time capable of being manipulated to uncouple the things from each another.

As used herein, the term "configure" or "configuration" means to design, arrange, set up, or shape with a view to specific applications or uses. For example: a military vehicle that was configured for rough terrain; configured the computer by setting the system's parameters.

As used herein, the term "substantially" refers to something which is done to a great extent or degree; for example, "substantially covered" means that a thing is at least 95% covered.

As used herein, the term "alignment" refers to the spatial property possessed by an arrangement or position of things in a straight line or in parallel lines.

As used herein, the terms "orientation" or "position" used interchangeably herein refer to the spatial property of a place where or way in which something is situated; for example, "the position of the hands on the clock."

As used herein, the terms "thermal conductance" or "conductance" refers to the ratio of thermal conductivity of a layer to its thickness.

DETAILED DESCRIPTION OF THE INVENTION

The present invention provides a non-invasive monitoring device to check the possibility of thermal stress of a user. In addition, the present invention provides a method to monitor thermal stress of a user of the device of the present invention. The user may use such a device while in environments they wish to work in, engage in athletic activities, or otherwise be present. Such a device and method of monitoring may be especially useful in environments and conditions where a user may be at higher risk for thermal stress. The materials and configuration of the device, and its method of use, are uniquely designed to more accurately account for the conditions in which thermal stress may be a danger. For example, such a device may be useful in helping firefighters monitor themselves for heat stress when fighting a blaze while wearing full-protective gear. Similarly, such a device may be useful in helping athletes to monitor themselves for heat stress while exerting themselves on a hot and humid day. Such a device may help a commercial fisherman in the cold and wet environment to monitor themselves for the onset of hypothermia. Likewise, such a device may help any workers to monitor themselves for thermal stress in the particular environment in which they must work.

To gain a better understanding of the non-invasive thermal stress monitoring device, attention is directed to the Figures of the present specification. FIG. 1 shows an expanded view of a non-invasive thermal stress monitoring device 10. The thermal stress monitoring device 10 has two basic parts, a monitoring unit 20 and a cover 30. The monitoring unit 20 contains the basic inner working of the thermal stress monitoring device 10 and the cover 30 serves to hold the monitoring unit 20 in place during use.

As is shown in FIG. 1, the monitoring unit 20, has substrate 21, the substrate has a first side 22 and a second side 23. The first side 22 of the substrate 21, for purposes of discussion is the user facing side of the substrate 21. Attached to the substrate 21 are temperature sensors 25. As show in FIG. 2, the temperature sensors are present on both the first side 22 and the second side 23 of the substrate 21. The temperatures sensors 25 on the first side 22 serves to provide a temperature reading of the skin of the user, while the temperature sensor 25 on the second side of the substrate serves to provide a temperature reading away from the skin of the user. The purpose of having temperature sensors 25 on both sides 22, 23 of the substrate 21 will be explained in more detail below. Other features present in the monitoring unit are a processor 26 (shown in FIG. 1), a power supply 27, an alert mechanism or alarm 28 and an optional cover 29. Optionally, the first side 22 of the substrate may have a material which will make the device of the present invention to be comfortable for a user to wear. For example, the first side of the substrate may have a soft to the touch surface material applied to the first side of the substrate.

Figure 5:
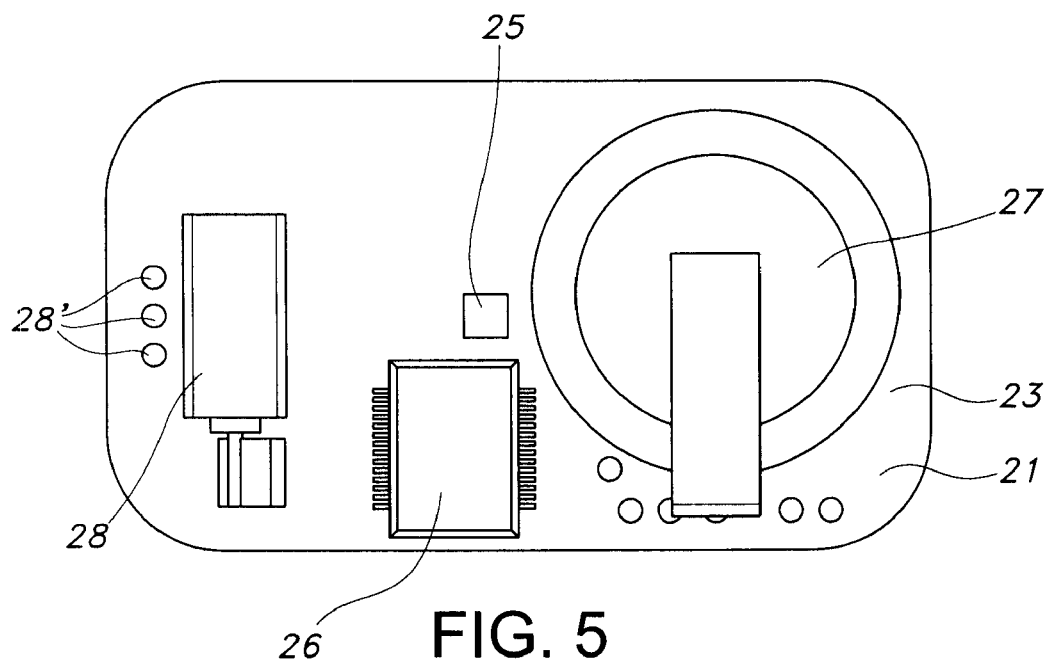
FIG. 5 shows a second side view of the substrate with the processor, power supply, temperature sensor and alert mechanisms FIG. 6 show a first side view (body facing side) of the substrate with temperature sensors.
Figure 6:
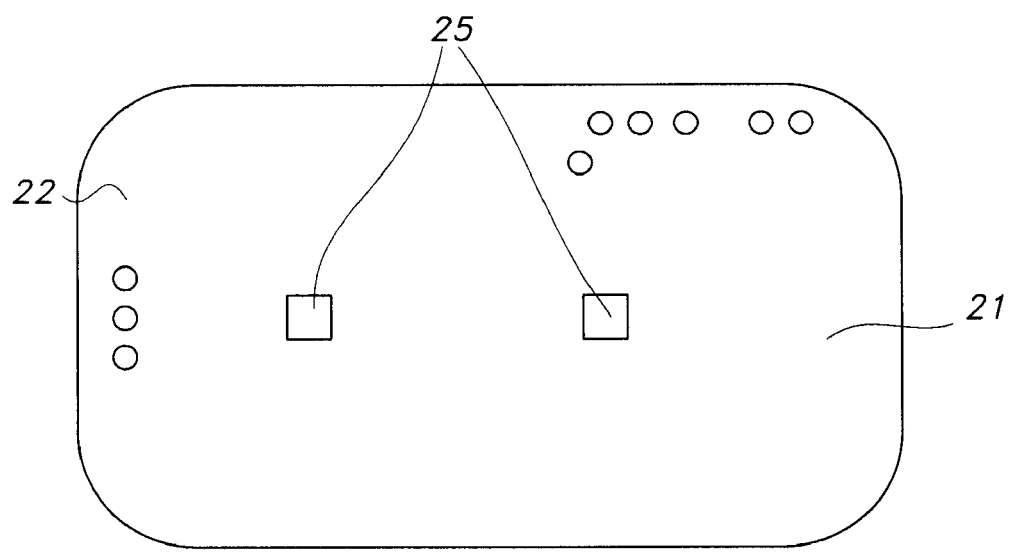

FIGS. 5 and 6 show a possible configuration of the different components on the substrate 21. FIG. 5 shows the second side 23 of the first substrate having the power supply 27, temperature sensor 25, processor 26, and two alarms 28 and 28'. Alarm 28 as shown in FIG. 5 is shown as a tactile alarm, which cause vibration when activated. Alarm 28' is a series of visual alarms, such as LED lights. FIG. 6 shows a possible configuration of the temperature sensors 25 located on the first side 22 of the substrate 21

The substrate 21 should be a prepared from a material which is a thermal insulating material. To effectively estimate the core body temperature, two temperature measurements are necessary, one at the skin surface of the user and a second at a fixed distance from the skin of the user and through an insulating material of known thermal properties used as the substrate. Substrate 21 should have a known thermal conductivity value so that the heat flux across the substrate can be determined, which in turn allows the thermal stress monitoring device to process the temperature reading to make a determination as to whether or not the user is under thermal stress. In addition, depending on the size of the monitoring unit 20, the substrate may be prepared from a flexible or an inflexible material. The larger the monitoring unit 20, the larger the need for the substrate 21 to be flexible. The smaller the monitoring unit 20, there is less need for the substrate 21 to be flexible. This is primarily driven by the need to maintain good contact with the skin and facial contours. Such contact is essential to minimize the measurement error in the skin temperature.

Generally, substrate 21 may be a single layer or multilayer substrate. In the case of a multilayer substrate, one of the layers of the multilayer substrate may be a thermal insulation material, which may include a soft rubber-like material such as neoprene or vulcanized rubber. The second layer of the multilayer substrate may be a flexible circuit board. When the substrate 21 is a single layer structure, the substrate may be a circuit board. One particular example of a suitable material which may be used to prepare the substrate 21 is an epoxy resin, such as an FR-4 circuit board. FR-4 circuit board is essentially a rigid structure and is an epoxy resin reinforced with a fiberglass mat. Although the FR-4 circuit board is essentially rigid, as is stated above, less flexible materials may be used as the substrate 21 when the monitoring unit 20 has an overall relatively small size. Further, having a substrate 21 which is a single layer, there is less of a chance that the substrate will delaminate during use. Generally, the substrate layer 21 should have a thermal conductance in the range of 32 to 1200 (W/m$^2$ K).

On each side of the substrate 21, present are temperature sensors 25. That is, the first side 22, or body facing side of the substrate 21 has at least one temperature sensor 25 and the second side 23 of the substrate has at least one temperature sensor. Suitable temperature sensors included, for example, a thermistor in either a Wheatstone Bridge configuration or a simple voltage divider configuration, the p-n junction of a very inexpensive rectifier diode, or a solid state temperature sensing integrated circuit such as the ADT75 or ADT7302 both produced by Analog Devices Corporation.

Figure 2:
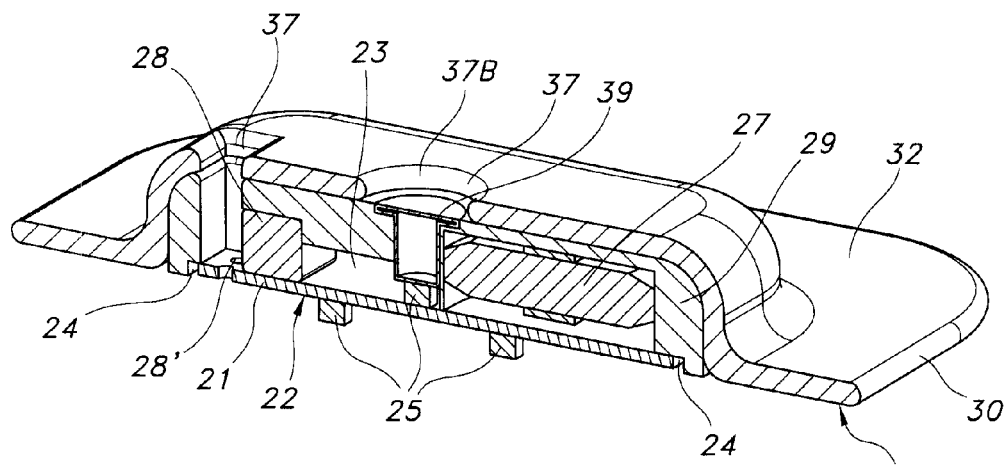
FIG. 2 shows a cut-away view an exemplary thermal stress monitor device within the scope of the present invention.

Generally, the first side 22 of the substrate 21 will have two or more temperature sensors 25 to ensure that the monitoring unit 20 is receiving a proper temperature reading from the sensors and that at least one temperature sensor 25 is properly placed on the user. Properly placed as used here refers to the spatial location which should be as close to the temporal artery as possible. See FIG. 6. As for the temperature sensors 25 on the first side 22 of the substrate, the temperature sensors 25 should be positioned such that the temperature sensors 25 extend away from the first side 22 of the substrate 21. That is, as is shown in FIG. 2, the temperature sensors 25 of the first side 22 of the substrate 21 will extend from the first side 22 of the substrate 21 so that they will effectively contact the skin of the user. By having temperature sensors 25 present on both the first side 22 of the substrate 21 and the second side 23 of the substrate 21, the heat flux through the substrate 21 can be effectively measured. More than one temperature sensor 25 may be present on the second side 23 of the substrate 21.

The temperature sensors 25 convey temperature information to a processor 26 present within the monitoring unit 20. The processor 26 is configured to perform the tasks of collecting temperature data from the multiple temperature sensors 25 present within the monitoring unit 20. Generally, the processor 26 is attached to the substrate 21, as is shown if FIG. 5 or can be optionally attached to another portion of the monitoring unit 20, provided that the temperature sensors 25 are electrically connected to the processor 26. Temperature data from the temperature sensors 25 are provided to the processor via either by analog to digital converter input channels or serial communication busses providing RS-232, SPI, or I$^2$C communication capabilities. In addition, the processor 26 processes the temperature data, determines whether a thermal stress alarm is needed and outputs an alarm signal, if necessary. The processor 26 is generally a low-power processor since processing power requirements are low and, as a result, heat generation will be relatively low. The processor 26 collects data from the multiple temperature sensors 25 on a fixed time interval and implements an algorithm to predict the core body temperature. Several core temperature values are maintained in a first-in-first-out (FIFO) data buffer to facilitate calculations in estimating a temperature change over time. Examples of possible processors include the MSP430 Ultra-low Power Microcontroller available from Texas Instruments (Dallas, Tex.) or the PIC16F689 8-bit PICO Microcontroller available from Microchip Technology, Inc. (Chandler, Ariz.).

An alert mechanism or alarm 28 is also present within the monitoring unit 20. The alarm mechanism 28 may include any means that stimulates one of the human senses to gain the attention of the user. For example, the alert mechanism 28 may include an audible alarm, a visual alarm, a tactile alarm or a combination of these alert mechanisms. Audible alarms are alarms which will attract the attention of the user or others around the user via hearing and include, for example, a tone generator, playback of a stored spoken message, a piezoelectric buzzer, or other similar alarms that will attract the user's attention by hearing. Tactile alarms are alarms which will alert user by the sense of feeling through the skin of the user such as a vibration. Visual alarms are alarms which will attract attention of the user or others near the user by visual means. Visual alarms include, for example, a blinking light, colored LEDs (light emitting diodes), an alpha-numeric display, or other similar alarms to attract the user's attention by vision. The alert mechanism may include a combination of any, or all, such alarms. For example, the alarm may include a blinking colored LED along with a vibrating piezoelectric buzzer. Alternatively, the alarm 28 may include a tone generator along with an LED display that displays the determined body core temperature. The alarm 28 should be capable of notifying the user of the alarm condition, but must also only consume minimal amounts of power.

As is shown in FIG. 5, visual alarms 28' may be a series of LEDs which may be on the second side of the substrate 21.

In one optional embodiment, the thermal stress monitoring device 10 may provide different alerts based upon specific thresholds. In addition to the threshold core temperature range and threshold change in core temperature range, the device may include stored warning ranges. Such warning ranges may be core temperatures or changes in core temperature within the threshold ranges, but may be included to warn the user of situations where the user's core temperature and/or change in core temperature is approaching the limits of threshold ranges. When the limits of such warning ranges were crossed, the device would then create a warning signal. The warning signal would then trigger a warning alarm. Such a warning alarm may utilize the same alarm utilized for the previously discussed threshold range alarm, it may use such a threshold alarm in a different way, it may utilize a warning alarm device separate from the alarm device for the threshold range alarms, or may use some combination thereof. For example, the thermal stress monitoring device may include a series of differently colored LEDs such that a warning alarm may be signaled by a yellow LED and a threshold range alarm may then be signaled by a red LED. In an alternate example, the warning alarm may include a blinking light and an audible beep every 30 seconds and if the threshold range is exceeded the light may switch to a more rapid blinking, the beep may become a sustained tone, and an additional alert signal may be sent to a remote alarm device. One skilled in the art would understand that various types and executions of warning alarms and threshold range alarms may be utilized to meet the particular needs of various users and environments of use.

In addition to the various types of alarms that may be utilized, in some optional embodiments, the alarm device 10 may continue to produce its alarm until the monitoring device determines that the core temperature, or change in core temperature, returns to within the appropriate threshold range. Alternatively, the alarm device may continue until the alarm device is reset. Such a reset may be included in the alarm device and may be reset by the user or may be configured such that the alarm may only be reset by another person (e.g., by a supervisor, safety officer, or a trainer). In another optional embodiment, the alarm may be reset only by relocating the user (and device) to a different location. Such alarm resets may be any combination of such options as desired by the particular user needs and/or particular safety accountability desired.

In a further optional embodiment of the present invention, the device could activate another device that could help address the thermal stress condition that may affect the user. For example, the alarm device could activate a personal cooling fan or personal cooling device which may be connected to the thermal stress monitoring device of the present invention. This could help reduce the users core body temperature and potentially reduce the onset of thermal stress in a user.

To power the monitoring unit 20, a power supply 27 is present. The power supply 27 can take on many forms. The power supply 27 may be disposable or rechargeable. Additional criteria for the selection of the power supply device allow for the device to be disposable without contaminating the environment and provide sufficient power to supply the device for the entire useful life of the product. Examples of such power sources include, a lithium-ion coin cell battery, flexible thin film batteries, super capacitors, or one of several available energy harvesting devices coupled with a storage capacitor. The actual type of power supply used in the monitoring unit 20 is not critical to the present invention, provided that the power supply does not generate too much heat during use, which could adversely effect the ability of the thermal stress monitor from properly operating during use.

The monitoring unit 20 may optionally have a shell 29 which covers the internal component of the monitoring unit, including the temperature sensor 25 on the second side 23 of the substrate 21, the processor 26, the alert mechanism 28, and the power supply 27. Generally, the shell 29 is a hard component which encases and will protect the internal components from dust, debris and the like before, after, and during use. The shell 29 will also protect these internal components from damage by the user before, during, and after use, including, for example, damage caused by an impact to the monitoring unit 20. Generally, shell 29 will have a size and shape to protect the internal components and can be configured to connect on the sides 24 of the first substrate 21. The shell 29 and substrate 21 could have complementary fasteners or fastener means (not shown) so that the shell 29 will be held in place by the substrate 21. Suitable fasteners include, for example notches and slots, a screw or other similar fasteners. The fasteners should be selected, depending on the intended use of the monitoring device. For example, if the monitoring device is reusable, then a removable fastener could be used. That is, if the monitoring device is intended to be reusable, it would be advantageous to make the cover removable so that components, such as the power supply 27 could be removed and replaced to extend the life of the monitoring device 20. On the other hand, if the monitoring device is intended to be disposable, then a more permanent mounting may be used.

Figure 3:
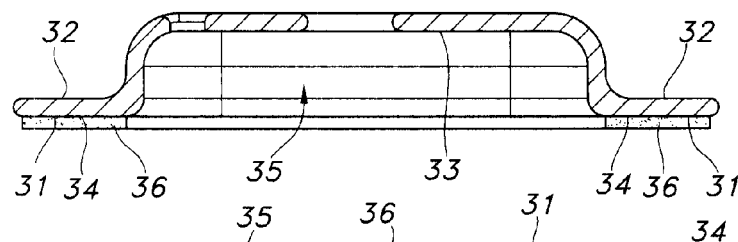
FIG. 3 shows a cross-section of the cover.
Figure 4:
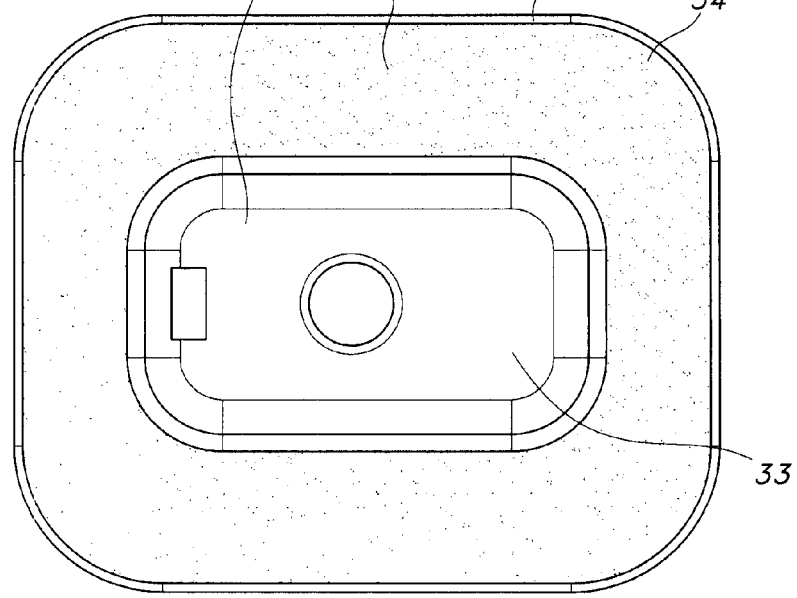
FIG. 4 shows a bottom view of the cover.

The cover 30 is effectively used to hold the monitoring unit 20 in place on a user during use. The cover 30 has a first side 31 and an opposite second side 32, as is shown in FIGS. 1, 2 and 3. As shown, the first side 31 is the user-facing side of the cover 30 and the second side 32 faces away from the user during use. The first side 31 of the cover 30 has a defined area and this defined area has a first area 33 and a second area 34, as shown in FIG. 4. Adapted or configured to receive the monitoring unit 20, first area 33 will generally have a shape or configuration that conforms to the shape and/or configuration of the monitoring unit 20. For example, as shown in FIGS. 3 and 4, the cover 30 has a recessed region 35 which is approximately the same size and shape as the monitoring unit 20, so that the monitoring unit 20 will fit into the recessed region 35. Generally, the recessed area 35 should be a size and shape such that the monitoring unit 20 is not readily removed from the cover 30 during normal handling of the monitoring device 10; but the size and shape of the recessed area 35 should be such that the monitoring unit 20 can be removed from the cover 30 after use by the user or by another person. Ideally, the monitoring unit 20 and cover 30 are complementary sized such that the monitoring unit 20 fits snuggly into the recessed region 35 of the cover 30. Alternatively, the recessed region 35 could be larger than the monitoring device 20 and an adhesive or other attachments means could be used to hold the monitoring unit 20 within the recessed region 35 of the cover 30.

As shown in FIG. 4, the cover 30 is rectangular in shape; however, this shape is only intended to be exemplary. Other shapes can be used for the cover 30, so long as the selected shape is larger than the monitoring device 20 and the shape can accept and hold the monitoring unit 20 in place on a user. For example, the cover can be circular, elliptical, square or any other shape, so long as the cover 30 is adapted to receive the monitoring unit 20.

The first side 31 of the cover 30 has a second area 34. The second area 34 of the cover generally serves to provide for a means for attachment of the thermal stress monitoring device 10 to the skin of the user. One way to affix the thermal stress monitoring device 10 is to use a pressure sensitive adhesive 36 applied to a least a portion of the second area 34 of the cover 30. The pressure sensitive adhesive may cover the entire second area 34 or may be applied in a portion of the second area 34. The pressure sensitive adhesive 36 may be applied as a uniform coating, in a set pattern or randomly in the second area 34. Essentially, the pressure sensitive adhesive can be any pressure sensitive adhesive which will release from the skin of the user in the area in which the thermal stress monitoring device 10 is applied while maintaining good adhesion even when the wearer is sweating. Suitable pressure sensitive adhesives included, for example, medical grade pressure sensitive adhesives, such as Product #1524 Medical Transfer Adhesive and Product #9917 Medical Nonwoven Tape both available from 3M. Other means to affix the thermal stress monitor to the user include, for example clipping on to another product such as hard hat, welding helmet or pressed against the skin or attached to a sweatband worn around the head. In addition, the pressure sensitive adhesive 36 may be covered with a release sheet (not shown), which is removed prior to use. The release sheet can help maintain the adhesive nature of the adhesive 36 prior to use, by preventing dirt, dust and/or debris from attaching to the adhesive 36 prior to use.

Suitable release sheets include webs of material coated with a release coating, such as a silicone coating. One particularly suitable release sheet is a paper substrate coated with a silicone release coating. The release coating should be selected so as not to interfere with the adhesive properties of the pressure sensitive adhesive prior to use, for example during storage.

Generally the cover 30 is prepared from a flexible material that provides that also provides insulative properties. By flexible, it is intended that the material used for the cover may be subjected to forces which will bend or twist the cover 30, but the cover 30 essentially returns to its original shape and size. Suitable materials which may be used to form the cover include polyurethane, silicones, elastomeric polyolefins and thermoplastic elastomers. The material selected for the cover should be flexible enough to conform to the skin and facial contours of the user. By using a flexible material for the cover, the cover may be flexed to remove the monitoring unit 20 from the cover 30 after use.

The cover 30 may have one or more openings or apertures 37 therein as shown in FIG. 2. As shown in FIG. 1, there are two opening 37A and 37B. Opening 37A may be present so that when the alert mechanism 28 is a visual alarm 28', such as an LED, and the visual alarm is present on the substrate 21 of the monitoring unit 20, the visual alarm will be visible outside of the cover 30. Alternatively, the opening 37A may be covered with a transparent piece (not shown) which will protect the visual alarm, from damage and debris during use. In one embodiment, the transparent piece may provide magnification, so that the visual alarm is more visible outside of the cover 30.

As shown in FIGS. 1 and 2, opening 37B is provided to allow for the temperature sensor 25 on the second side 23 of the substrate 21 take a combined temperature reading; taking into account with the internal temperature of the monitoring unit 20 and the ambient temperature of the external environment outside of the thermal stress monitoring device 10. The combined temperature reading allows the thermal stress monitoring device 10 to estimate the heat flux from the body of the user that is occurring by the users natural body processes. The temperature sensor 25 on the second side 23 of the substrate 21 may be left open to the external environment or may be connected to the external environment via a thermally conductive member 39, which is also called a heat transfer pipe. That is the thermally conductive member extends through the cover 29 and the shell 30, when either one of the cover and/or shell are present.

The heat transfer pipe 39, is prepared form a thermally conductive material that will be able to transfer heat to and from the temperature sensor 25. Examples of materials useable as the heat transfer pipe 39 include metals such as aluminum. The essential requirement for the heat transfer pipe is to have high thermal conductivity and low mass.

The cover 30 of the thermal stress monitoring device 10 may be reusable or may be disposable. In may be advantageous to make it disposable since the adhesive 36 used to attach the cover 30 to the skin of the user may become soiled with hair, skin oils, perspiration and dirt during use. As a result, to make the cover 30 effective for a second or subsequent use, the adhesive 36 may need to be removed and reapplied to the first side 31 of cover prior to a second or subsequent use. Alternatively, if the cover 30 is disposable, the cover can be replaced by the user before each use and the user will be confident that the cover will effectively hold the monitoring unit 20 in place during use.

To effectively estimate the core body temperature, two temperature measurements are necessary, one at the skin surface of the user and a second at a fixed distance from the skin of the user and through an insulating material such as the substrate 21. Substrate 21 should have a known thermal conductivity value so that the heat flux across the substrate can be determined, which in turn allows the thermal stress monitoring device 10 to process the temperature reading to make a determination as to whether or not the user is under thermal stress.

To understand the workings of the thermal stress monitoring device, the following is an explanation of heat flux and how it applies to thermal stress. The thermal stress monitoring device measures the heat flux leaving the body by measuring the temperature drop across a known thermal insulator having a low thermal conductance, in the case of the thermal stress monitoring device described here, the substrate 21 is the known thermal insulator. The device performance quality depends on balancing two factors. Temperature drop across the device must be large compared to the error in the temperature sensors. This puts constraints on the thermal conductance of the substrate 21. In addition, the heat flux through the thermal stress monitoring device 10 must be much larger than the heat flux moving around the device 10.

Figure 7:
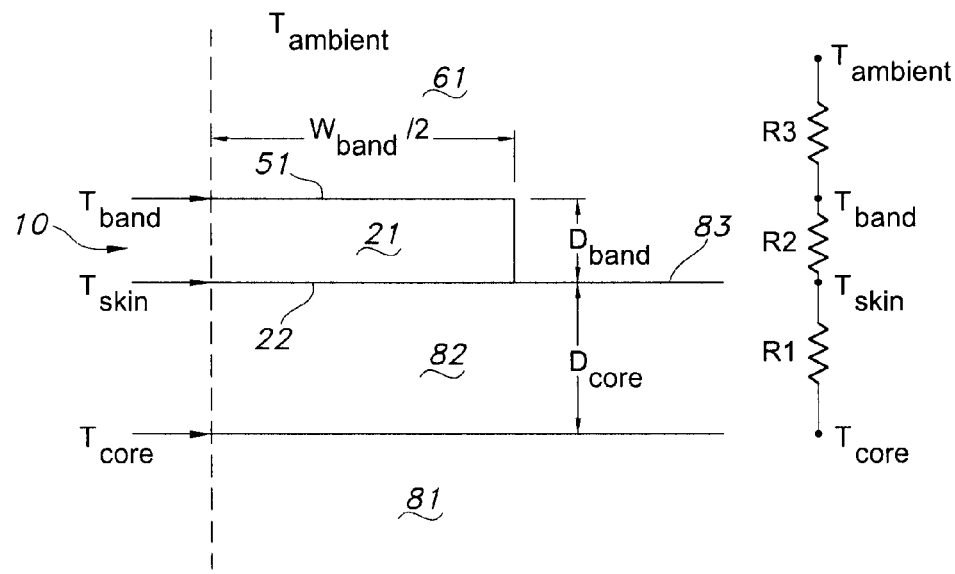
FIG. 7 shows a one-dimensional heat balance model used for determining parameters for thermal stress monitoring in accordance with devices of the prior art.

These design constraints can be characterized by equations describing the physical or statistical phenomena. FIG. 7 illustrates a model of the one-dimensional thermal balance. The one-dimensional steady state equation for core body temperature is given by equation (1).

$$T_{core} = T_{skin} + \frac{L_{band}}{L_{core}}(T_{skin} - T_{band}) \tag{1}$$

$T_{skin}$ is the temperature of the skin under the device 10 measured by temperature sensor(s) 25 on the first side 22 of the substrate 21. $T_{band}$ is the temperature measure on the second side 23 of the substrate 21 of the monitoring unit 20. $L_{band}$ is the thermal conductance of the substrate 21 or the ratio of the thermal conductivity to the layer thickness. Correspondingly, $L_{core}$ is the thermal conductance of the body of the user.

The movement of heat is analogous to the movement of electricity in a circuit. The series of resistors R1, R2, and R3 shown on the right side of FIG. 7 represent the one-dimensional heat movement through the various layers described on the left side of FIG. 7. Current flow in the electrical circuit is analogous to heat flow (Joules/second or Watts). The resistance in the circuit is analogous to the inverse of conductance. Just as a voltage drop across a finite resistance causes electricity to flow, temperature drop across a finite thermal resistance causes heat to flow. Conductance given in units of W/m² K would be the inverse of the resistance, given in units of m² K/W. Conservation of heat is analogous to conservation of current. Heat flow into and out of any point sums to zero just as the sum of current into and out of any point in a circuit sums to zero. This analogy must be used with care in the case where we make use of heat flux (W/m²). Heat flux accounts for the area through which the heat flows. The total heat flow is the product of the heat flux and the area through which it flows. Such distinction is necessary when considering the geometric effects of the device design. In FIG.7, R1 represents the resistance of the body to heat flow. R2 is the resistance of heat flow through the device 10, and R3 represents the resistance of heat flow to move from the outer surface 51 of the device 10 into the surrounding environment 61.

Using propagation of error for non-linear equations it is possible to create an approximate equation for error in $T_{core}$ as a function of error in the measurement of $T_{skin}$ and $T_{band}$. When the skin and insulator sensors are the same the errors for both can be assumed equal which leads to the following:

$$\sigma_{Tcore} = \sigma_{Tsensor}\sqrt{1 + 2\left(\frac{L_{band}}{L_{core}}\right) + 2\left(\frac{L_{band}}{L_{core}}\right)^2} \quad (2)$$

The ratio of $\sigma_{core}$ to $\sigma_{Tsensor}$ is measure of error amplification. Temperature sensors with an accuracy of 0.1° C. are typical. Choosing a value of 1° C. for the device accuracy would result in a ratio of 10.

The thermal conductance of the body ($L_{core}$) is treated here as a fixed value. Thermal conductance is the ratio of the thermal conductivity to the material thickness so variations in either the thermal conductivity or the depth of the core temperature zone would correspond to changes in the thermal conductance of the body. Thermal conductivity of various components of the human body varies as shown in Table 1 (see Herman I. P. *Physics of the Human Body*. Springer, Berlin, 2007. p. 362.). The body conductance of interest refers to the volume-weighted average of all the components of the body between the skin sensor and the layer in the body at the core body temperature.

TABLE 1

| Tissue | Thermal Conductivity (W/m K) | Specific Heat (MJ/m K) |
|---|---|---|
| Muscle-living | 0.642 | 3.94 |
| Skin - normal | 0.960 | 3.77 |
| Subcutaneous pure fat | 0.190 | 1.96 |
| Whole blood | 0.549 | 3.82 |

The depth ($D_{core}$) of the core body temperature depends on location on the body and differs subject to subject. It is possible to minimize the variation by choosing a location on the body where an artery is close to the surface of the body. The temporal artery is an ideal selection because variation in conductance is low. Experimental work was done to estimate a value for artery depth. A heat stress indicator device based on the design described in this patent was worn simultaneously with an ingestible core temperature sensor (Jonah capsule by Mini Mitter). It is possible to estimate the depth of the temporal artery using the core temperature measured by the capsule with the knowledge of the material properties of the device. A calculated value of 2.5 mm was determined for $D_{core}$.

As a person becomes more active and the core body temperature increases, vasodilatation occurs in the skin causing an increase in blood flow and an increase in thermal conductivity. The relationship between activity level, core body temperature, and thermal conductance is an important factor. Thermal conductivity of the skin for example changes from a value of 0.34 W/m K when cold to 0.96 W/m K when warm and even as high as 2.8 W/m K when very warm (see Robert A. Freitas Jr., Nanomedicine, Volume I: Basic Capabilities, Landes Bioscience, Georgetown, Tex., 1999, Table 8.12). Near the temporal artery, values of body conductance are expected to be between 20 and 200 W/m² K. In practice, the device would select a conductance value appropriate to the physiological state of the wearer.

The equation for estimating core temperature based on the one-dimensional model is given in equation (1). A generalized form of equation (1) may be shown as:

$$T_{core} = T_{skin} + A \cdot (T_{skin} - T_{band}) \quad (3)$$

The term 'A' being the ratio of the thermal conductance of the bandage to that of the core is therefore not strictly constant.

$$A = \frac{L_{band}}{L_{core}} \quad (4)$$

As the body heats up and vasodilatation occurs, the thermal conductance of the core increases and the value for 'A' is reduced. In practice values for 'A' would be chosen based on the physiological state of the subject. A look-up table can be produced by calculation based on blood perfusion as a function of core body temperature and the corresponding change in thermal conductance of the core layer ($L_{core}$). Alternately such a table could be derived from experimental data covering the range of subjects so as to provide a table of 'A' values applicable to the population of expected wearers.

Figure 8:
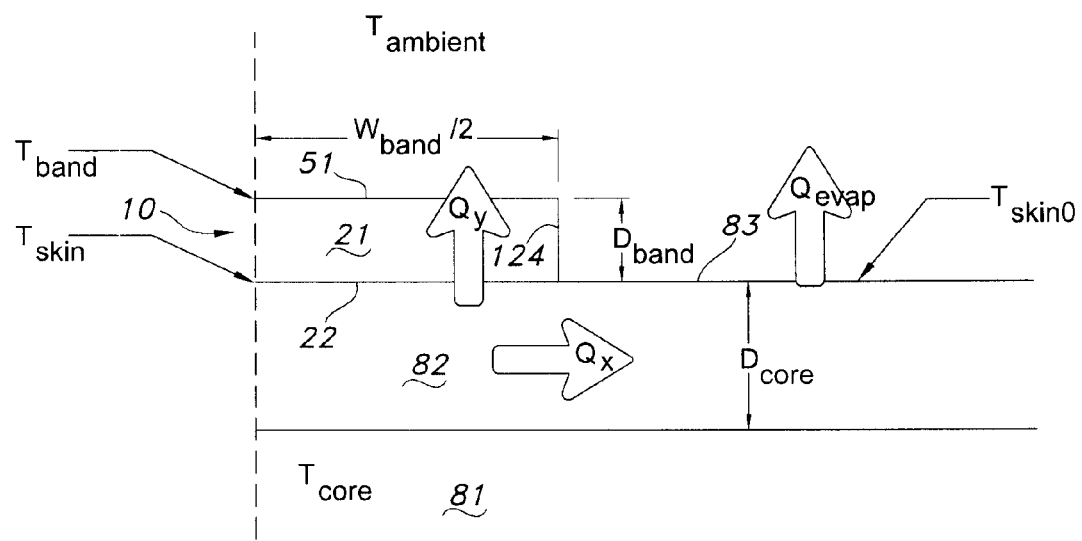
FIG. 8 illustrates a heat balance model used for determining parameters for thermal stress monitoring in accordance with the present invention.

Accounting for the heat loss around the heat stress indicator is an important factor when using the one-dimensional heat loss model. The accuracy of the one-dimensional model is dependent on an accurate estimate of heat flux from the body. One method for achieving this is to design the device with a thermal conductance that is large enough that the flux through the device is very close to the heat flux leaving the body. This necessarily requires a minimal heat flux around the device. In general terms, heat flux leaving the body can go through the device 10 or around the device 10. FIG. 8 shows a cross-section schematic model of the device 10 as applied to the body. The left side of FIG. 8 is an axis of symmetry. The bottom layer 81 represents the layer in the body that is at the core temperature. $Q_x$ is the heat moving around the device 10 in the body layer 82 between the skin surface 113 and the core temperature layer 81. $Q_y$ is the heat flow moving through the device 10. $Q_{evap}$ corresponds to any heat loss caused by evaporation of body moisture from exposed skin adjacent to the indicator. $T_{ambient}$ represents the temperature of the surrounding environment 61. $T_{band}$ and $T_{skin}$ are the temperatures of the outer surface 51 of the device 10 and skin side surface 22 (first surface) of the substrate 21 in the device 10, respectively. $T_{core}$ is the core body temperature and $T_{skin0}$ refers to the skin temperature at a point 83 on the skin just outside the perimeter of the device 10. It should be recognized that $T_{skin0}$ is lower than $T_{skin}$ because of the insulation layer in the device. Sweat produced by the body is prevented from evaporating under the device, but is unhindered outside the device causing a further reduction in skin temperature. The difference in skin temperature under the device from that just outside the device causes a heat flow in the direction indicated by $Q_x$. When the heat flux around the device ($Q_x$) is large with respect to the heat flux through the device ($Q_y$) the one-dimensional model fails to estimate core body temperature accurately.

Figure 9:
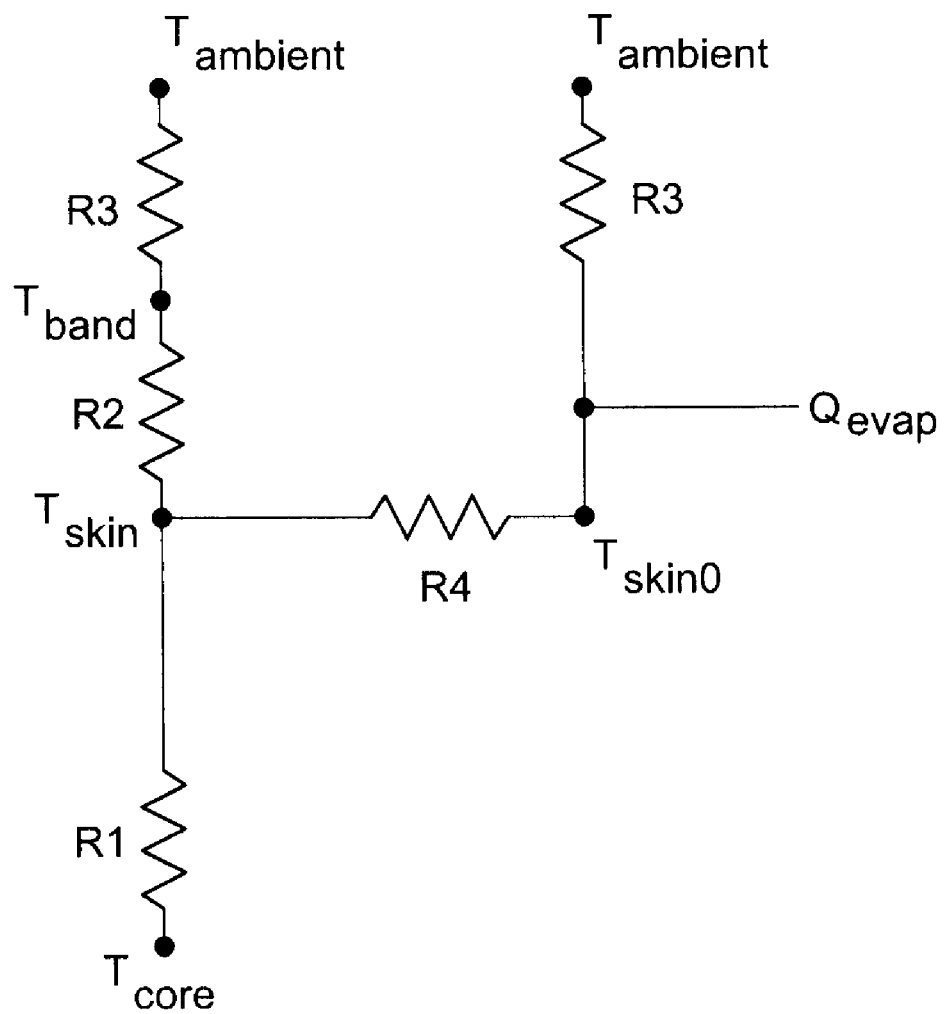
FIG. 9 illustrates a circuit diagram representative of the heat balance model of FIG. 8, in accordance with the present invention.

The drawing in FIG. 9 provides an analogous electrical circuit schematic for the geometry shown in FIG. 8. In the schematic of FIG. 9, R1 corresponds with the thermal resistance of the body, R2 corresponds with the thermal resistance of the device 10, and R3 corresponds with the resistance of heat leaving the surface 51 of the device into the surrounding environment 61. The resistor R4 represents the thermal resistance of the body around the device. The term $Q_{evap}$ corresponds to evaporative heat loss and is analogous to a specified current drain in the circuit. In this system the heat flow leaving the core may be written as:

$$Q_y = k_{core} \cdot \frac{W_{band}}{2} \frac{(T_{core} - T_{skin})}{D_{core}} \quad (5)$$

Where $k_{core}$ is the thermal conductivity of the body layer 101, $T_{core}$ and $T_{skin}$ are the core and skin temperatures respectively, and where $D_{core}$ is the depth to the core body temperature layer 101. The heat flow $Q_y$ is in J/sec or watts. Referring again to FIG. 8 the term $W_{band}/2$ is the distance between the sensor measurement of $T_{skin}$ and/or $T_{band}$ and the outer or peripheral edge 124 of the insulation layer/substrate 21. In the case that the measuring sensors are directly in the middle of the substrate 21, then $W_{band}$ would correspond to the minimum device width. For the sake of simplifying the discussion, $W_{band}$ is often referred to as the "width" of the device. However, for devices in which the measuring sensor(s) are not in the geometric center of the insulating layer, $W_{band}/2$ is the distance the sensors are from the peripheral edge 124 of the insulating layer/substrate 21.

The heat flow moving around the device ($Q_x$) is approximately:

$$Q_x = k_{core} \cdot D_{core} \frac{2 \cdot (T_{skin} - T_{skin0})}{W_{band}} \quad (6)$$

Where $T_{skin0}$ is the temperature of the skin at the outside edge of the device 10. The heat flow $Q_x$ is in J/sec or watts.

Approximate values for $T_{skin}$ and $T_{skin0}$ can be calculated by considering the steady state condition at two different locations. We will consider the case where the heat flux through the body layer is the same as the flux through the device, which is in turn equal to the heat lost into the environment 61.

$$\frac{k_{core}}{D_{core}}(T_{core} - T_{skin}) = \frac{k_{band}}{D_{band}}(T_{skin} - T_{band}) = h(T_{band} - T_{ambient}) \quad (7)$$

device 10 is proportional to the difference in the outer surface 51 temperature ($T_{band}$) and the outside temperature ($T_{ambient}$). The proportionality constant (h) is a transfer coefficient and has a value of approximately 9 W/m K, for people in nominal inside work conditions. Solving these equations provides a direct expression for $T_{skin}$ and for $T_{band}$.

$$T_{skin} = \frac{D_{core} \cdot h \cdot k_{band} \cdot T_{ambient} + k_{core} \cdot T_{core}(D_{band} \cdot h + k_{band})}{D_{core} \cdot h \cdot k_{band} + k_{core} \cdot (D_{band} \cdot h + k_{band})} \quad (8)$$

$$T_{band} = \frac{D_{core} \cdot h \cdot k_{band} \cdot T_{ambient} + D_{band} \cdot h \cdot k_{core} \cdot T_{ambient} + k_{band} \cdot k_{core} \cdot T_{core}}{D_{core} \cdot h \cdot k_{band} + D_{band} \cdot h \cdot k_{core} + k_{band} \cdot k_{core}} \quad (9)$$

At steady state and at a distance away from the device the heat flux leaving the skin 83 is equivalent to the heat entering the surrounding environment plus the heat lost from evaporation.

$$\frac{k_{core}}{D_{core}}(T_{core} - T_{skin0}) = h(T_{skin0} - T_{ambient}) + Q_{evap} \quad (10)$$

Rearranging this equation produces an expression for $T_{skin0}$.

$$T_{skin0} = \frac{k_{core} \cdot T_{core} + D_{core} \cdot h \cdot T_{ambient} - D_{core} \cdot Q_{evap}}{D_{core} \cdot h + k_{core}} \quad (11)$$

Substituting the expressions for $T_{skin}$, $T_{band}$, and $T_{skin0}$ (equations 8, 9, and 11) into equations (5) and (6) and simplifying produce the following:

$$Q_x = \frac{2 \cdot D_{core}^2 \cdot k_{core}(D_{core} \cdot h \cdot k_{band} \cdot Q_{evap} + k_{core}(k_{band} \cdot Q_{evap} + D_{band} \cdot h \cdot (Q_{evap} + h(T_{core} - T_{ambient})))))}{(D_{core} \cdot h + k_{core})(D_{core} \cdot h \cdot k_{band} + k_{core}(D_{band} \cdot h + k_{band})) \cdot W_{band}} \quad (12)$$

And $$Q_y = \frac{h \cdot k_{band} \cdot k_{core} \cdot W_{band}(T_{core} - T_{ambient})}{2(D_{core} \cdot h \cdot k_{band} + k_{core}(D_{band} \cdot h + k_{band}))} \quad (13)$$

Thermal conductance of the core ($L_{core}$) is the ratio of the bodies thermal conductivity ($k_{core}$) to the depth ($D_{core}$) of the The ratio of the heat flows $Q_x/Q_y$ can be simplified to the following expression:

$$\frac{Q_x}{Q_y} = 4 \cdot \frac{D_{core} \cdot h \cdot k_{band} \cdot Q_{evap} + k_{core} \cdot (k_{band} \cdot Q_{evap} + D_{band} \cdot h \cdot (Q_{evap} + h \cdot (T_{core} - T_{ambient})))}{h \cdot k_{band} \cdot (D_{core} \cdot h + k_{core})(T_{core} - T_{ambient})} \cdot \left(\frac{D_{core}}{W_{band}}\right)^2 \quad (14)$$

core temperature zone 81. Similarly the conductance of the insulation ($L_{band}$) is the ratio of the thermal conductivity ($k_{band}$) of the substrate 21 to its thickness ($D_{band}$). The heat lost into the environment 61 from the outer surface 51 of the This expression can be further simplified by considering the case where the core body temperature ($T_{core}$) is at 36.8° C., the ambient environment temperature ($T_{ambient}$) is at 27° C., the transfer coefficient (h) is 9 W/m K, the core body depth ($D_{core}$) is 0.0025 m, and the thermal conductivity of the body ($k_{core}$) is at 0.43 W/m K. The resulting simplified equation (14) for the ratios of heat flows is:

$$\frac{Q_x}{Q_y} = 4\left(\frac{7.209}{L_b} + \left(0.0118 + \frac{0.1101}{L_b}\right) \cdot Q_{evap}\right)\left(\frac{D_{core}}{W_{band}}\right)^2 \quad (15)$$

Equation (15) can be inverted to provide an estimated $W_{band}$ distance required to achieve a particular Q-ratio ($Q_x/Q_y$) or less.

$$Q_{ratio} = \frac{Q_x}{Q_y} \quad (16)$$

$$W_{band} > \frac{0.02 \cdot D_{core}\sqrt{72090 + 1101 \cdot Q_{evap} + 118 \cdot L_b \cdot Q_{evap}}}{\sqrt{L_b \cdot Q_{ratio}}} \quad (17)$$

The amount of error caused by heat flow around the device can be estimated by considering how the device would calculate core temperature. A device that uses the simple one-dimensional model uses the temperature drop across the insulation layer to estimate body heat flux. The general formula is equation (1). Excessive heat loss around the product causes the actual temperature drop across the insulation value to be reduced and the corresponding estimate of core body temperature to be low. The heat drop across an insulator is:

$$\Delta T = \frac{Q \cdot D}{k} = \frac{Q}{L} \quad (18)$$

Where 'k' is the thermal conductivity, 'D' is the thickness of the layer, and 'Q' is the heat flux. Consider the case where there is no added heat loss around the device.

$$\Delta T_{noloss} = \frac{Q_{band}}{L_{band}} \quad (19)$$

In the case where some of the heat flux is diverted around the device. The resulting flux through the device is reduced and the corresponding impact on the measured temperature drop would be:

$$\Delta T_{loss} = \frac{Q_{band} - Q_x}{L_{band}} \quad (20)$$

The error in core temperature estimation due to this diverted heat would be the difference between the temperature estimate with and without the diverted heat.

$$TcoreError = \left(T_{skin} + \frac{L_{band}}{L_{core}} \frac{Q_{band}}{L_{band}}\right) - \quad (21)$$
$$\left(T_{skin} + \frac{L_{band}}{L_{core}} \frac{(Q_{band} - Q_x)}{L_{band}}\right)$$
$$= \frac{Q_x}{L_{core}}$$

The combined constraints described in equations (3), (15) and (21) provide guidance for developing a heat stress indicator that accommodates some level of sweat loss from the skin around the device while remaining within given device accuracy targets.

Figure 10:
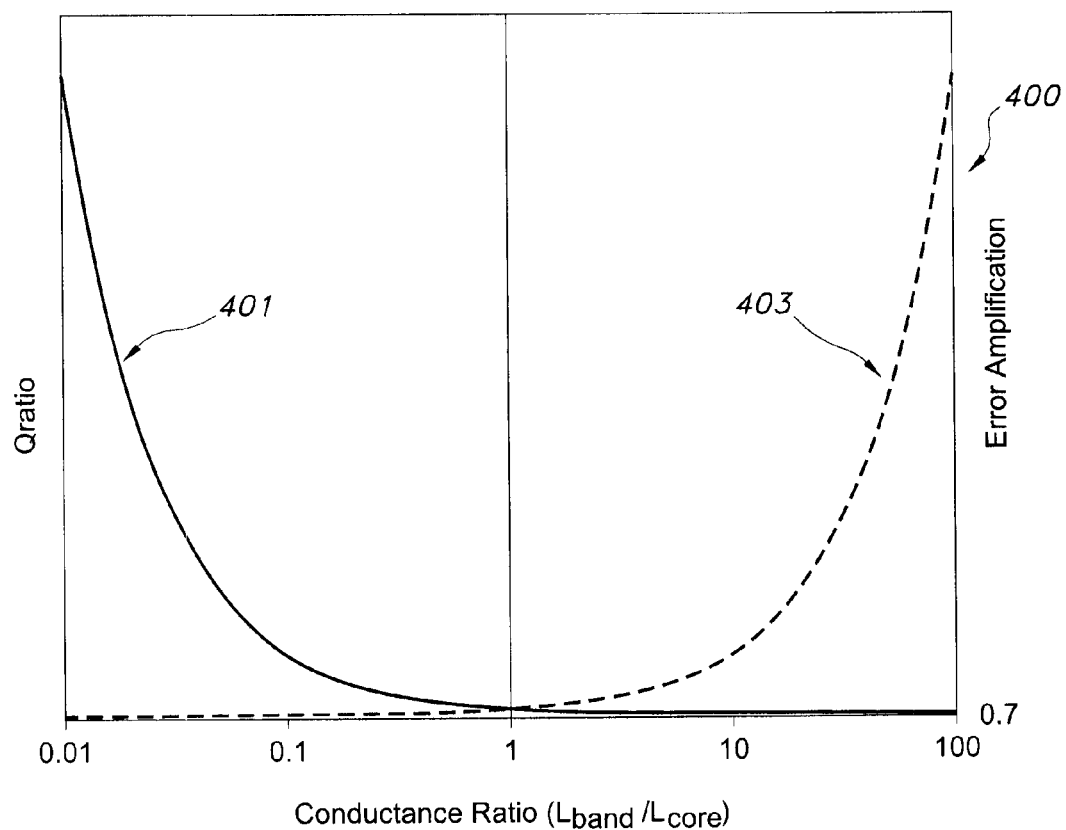
FIG. 10 is a plot that illustrates the optimization of the conductance ratio for the materials of the thermal stress monitoring device as a balance between device error and the heat transfer ratio as is in accordance with the present invention.

The design constraints are based on two design choices; the desire to use the one-dimensional model of heat flow and an overall accuracy target for the product. These constraints are characterized in FIG. 10 as two competing functions of the ratio of the thermal conductance of the device to the conductance of the body. This ratio 'A' as described in equation (3), has implications on error caused by the sensitivity limitations of the temperature sensing devices as described in equation (2). A reduction in the device thermal conductivity has a corresponding reduction in 'A'. At low thermal conductance, the temperature drop across the substrate 21 is maximized. The ratio of noise (i.e., the error from the temperature sensors) to the signal (i.e., the temperature drop across the substrate 21) is maximized and the error is minimized. This is shown as the "Error Amplification" curve 403 in FIG. 10. However, as 'A' is reduced corresponding to lower thermal conductivity of the device 10 less of the heat from the body is moving through the device 10 and more heat moves around it. This corresponds to an increase in $Q_{ratio}$ ($Q_x/Q_y$) as shown as the "Qratio curve" 401 in FIG. 10. The implication of FIG. 10 is that there is an optimum conductance ratio (A) for minimizing the two types of device error.

Figure 11:
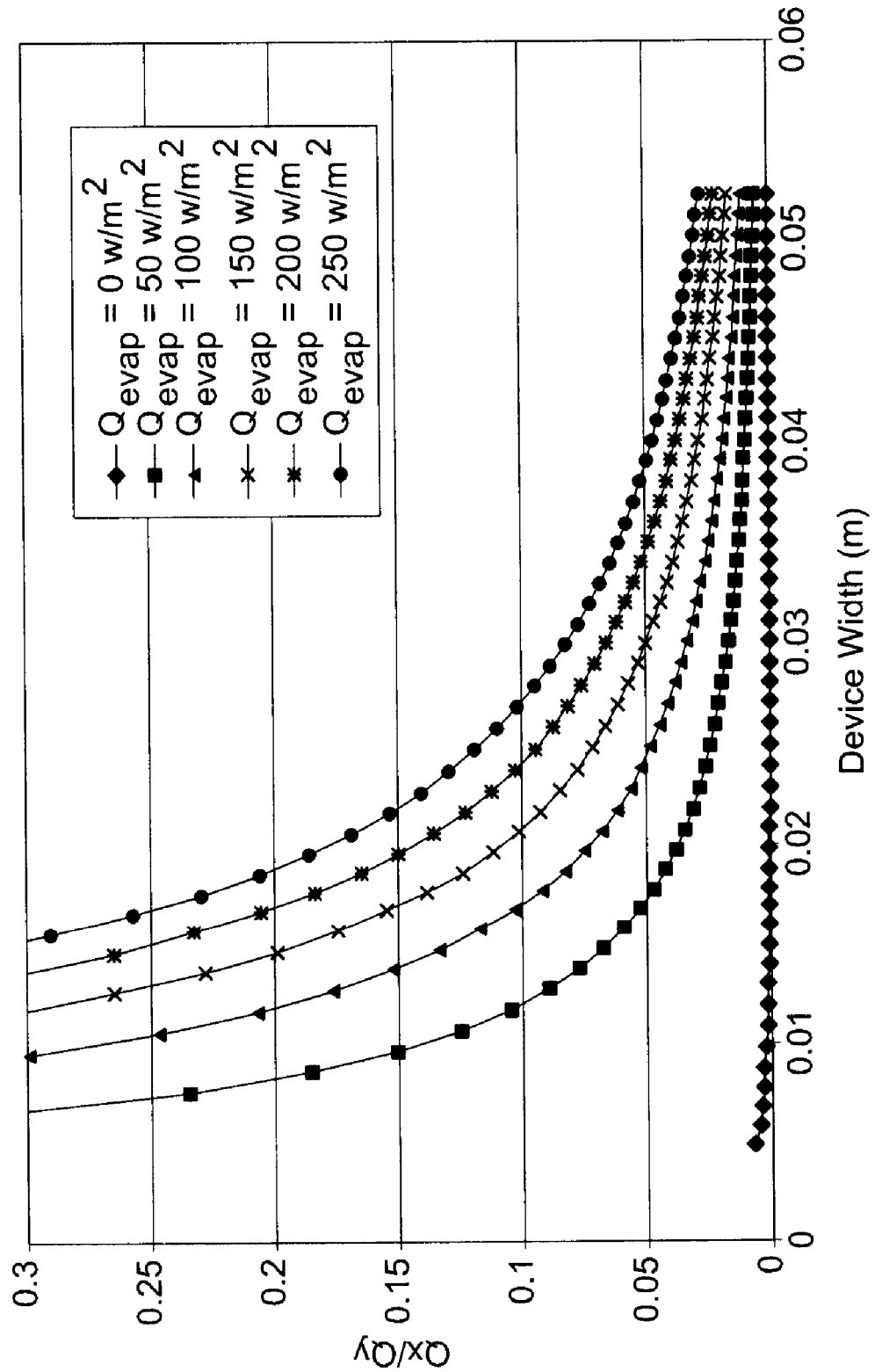
FIG. 11 is a plot that illustrates the selection of the device width in accordance with the present invention.

As described in equation (15), the ratio of heat flow around ($Q_x$) and through ($Q_y$) the device is a function of both the product width and the amount of evaporative heat loss on the skin. This relationship is shown graphically in FIG. 11 where the impact of evaporative heat loss is described for a device with a specified thermal conductance (where $L_{band}$=1127 W/m² K). This relationship demonstrates the ability to accommodate a given amount of evaporative heat loss by changing the size of the device. The appropriate choice of $Q_x/Q_y$ to minimize error requires some additional estimation as shown below.

The following provides an example of the combined use of these derived equations to develop size and material properties for a heat stress indicator. An estimate of body conductance is given by:

$$L_{core} = \frac{k_{core}}{D_{core}} \quad (22)$$
$$= \frac{0.43}{0.0025}$$
$$= 172 \frac{W}{m^2 \cdot K}$$

Here a volume weighted average for core thermal conductivity ($k_{core}$) is 0.43 W/m K and the depth of the temporal artery ($D_{core}$) is taken to be 2.5 mm. This value of $L_{core}$ can be substituted into equation (21). The value $T_{coreError}$ will be set to be about ⅓ of the tolerable error of 1° C.

$$TcoreError = \frac{Q_x}{172} \quad (23)$$

$$\frac{Q_x}{172} \leq 0.3 \quad (24)$$

$$Q_x \leq 52 \quad (25)$$

A reasonable upper end range for $Q_y$ is 250 W/m². This provides a rough estimate for an acceptable ratio of $Q_x$ to $Q_y$ at 0.21 or less. Non-acclimatized subjects working at a rate >65 W/m² are at the upper range of their thermal strain when sweating at 650 g/hr which corresponds to 250 W/m² of evaporative loss (see Doherty, T. J., and E. A. Arens. 1988. "Evaluation of the Physiological Bases of Thermal Comfort Models." ASHRAE Transactions, Vol. 94, Part 1, 15 pp).

Further, consider the case where the desired goal is for the error in core temperature estimates to remain at or below 1° C., and where the selected temperature sensors have an error of 0.1° C. Substituting these values into equation (2) generates the following:

$$10 \geq \sqrt{1 + 2\left(\frac{L_{band}}{172}\right) + 2\left(\frac{L_{band}}{172}\right)^2} \quad (26)$$

This equation is true when $L_{band} \leq 1127$ W/m² K. Neoprene has a nominal thermal conductivity of 0.2 W/m*K. A layer of neoprene 0.2 mm thick would provide such a thermal conductance. Alternately, a conventional circuit board material FR-4 which has a thermal conductance of about 292 W/m² K at 0.78 mm thickness is also a suitable material to use.

Substituting these values into equation (14) generates the following relationship.

$$0.21 = 4\left(\frac{7.209}{1127} + \left(0.0118 + \frac{0.1101}{1127}\right) \cdot Q_{evap}\right)\left(\frac{0.0025}{W_{band}}\right)^2 \quad (27)$$

As discussed earlier a value of 250 W/m² is a reasonable upper end value for $Q_{evap}$. Using this value of $Q_{evap}$ it is possible to solve for $W_{band}$. In this case the value is 0.019 meters, or just under 2 cm.

Thus, a thermal stress monitoring device containing sensors with a nominal accuracy of 0.1° C. sandwiched between a 0.2 mm layer of neoprene having a thermal conductivity of 0.2 W/m*K with no sensor nearer than 2 cm from any edge of the neoprene would maintain a core temperature error of less than 1° C. on a subject that is sweating at a rate such that 250 W/m² or less of evaporation was taking place around the device.

An alternate example could be a thermal stress indicator designed to less stringent evaporative heat loss values of 150 W/m². In this example, soft vulcanized rubber may be used and it has a nominal thermal conductivity ($k_{band}$) of 0.138 W/m K. Sensor accuracy of 0.1° C., and overall device accuracy target of 1° C. remain the same. The constraint from equation (2) provides a target insulator layer conductance at the same value of 1127 W/m² K. In the case of the rubber material this corresponds to a layer thickness of 0.005 inches. Making use of equation (15) this time with the reduced $Q_{evap}$ value of 150 W/m² generates a $W_{band}$ value of 1.46 cm. This example design maintains $T_{core}$ error at or below 1° C. for a subject sweating at or below 150 W/m² which corresponds to a moderate sweat level.

Figure 12:
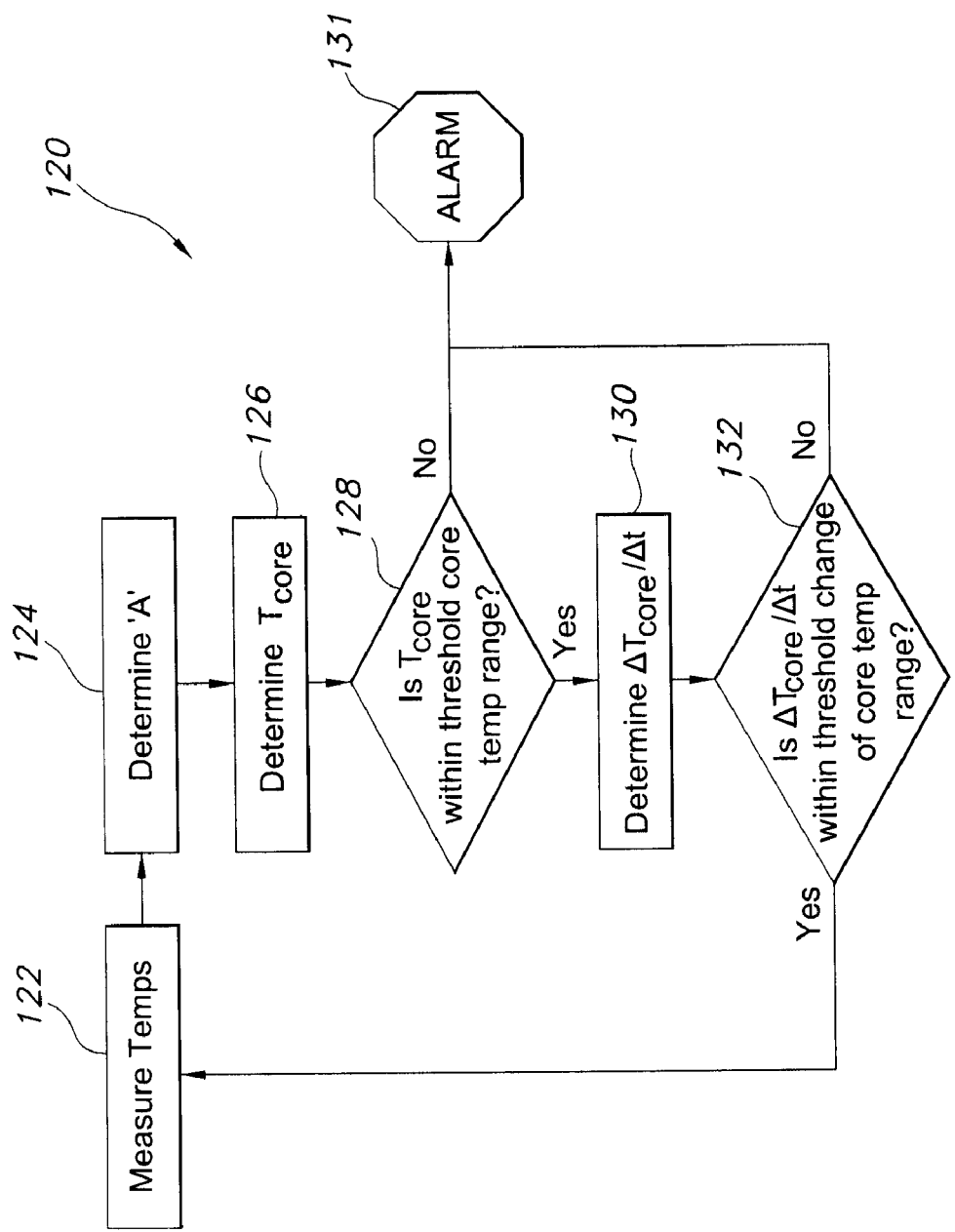
FIG. 12 illustrates a method for monitoring thermal stress in accordance with present invention.

In practice, the processor 26 of the thermal stress monitoring device 10 would execute a decision algorithm 120, such as illustrated in FIG. 12. As a first step 122, the temperature sensors 25 measure their respective temperatures. At step 124 the value of 'A', the ratio of insulating layer conductance to core conductance is determined, as discussed above. Next, in step 126 the core temperature is determined using equation (1). Then, in step 128, the determined core temperature is compared with a stored threshold temperature range. If the determined core temperature is outside of the threshold temperature range, an alert signal or alarm 131 is generated.

The stored threshold temperature range is the body core temperature range in which it is desired that the body core temperature is maintained. Such a threshold temperature range may include the limiters of standard temperatures given for heat stress and hypothermia. For example, the threshold temperature range may be 38° C. to 35° C. Such a threshold temperature range may be designed to be narrower or wider depending on when various thermal stress alerts may be desired.

Similarly, in step 130 the change in core temperature over a known period of time is determined. The determined change in core temperature from step 130 is then compared with a stored threshold change in core temperature range, in step 132. If the determined rate of change in core temperature is outside of the threshold rate of change of the core temperature, an alert signal 131 is generated.

The stored threshold change in core temperature range is the rate of change in the body core temperature in which it is desired to be maintained. Generally, the range will extend from zero to some maximum rate of change considered to indicate a thermal stress condition. For example, the threshold rate of change in body temperature range may be 0 to 1.5° C./hr.

The decision algorithm 120 would then return to step 122 and another set of temperature measurements would be collected, and the algorithm 120 would continue.

If either the determined core body temperature or the determined change of core body temperature over a fixed period of time falls outside the threshold ranges which indicate the onset of thermal stress, the microprocessor generates an alarm output 131. The thermal stress monitoring device may also include an alarm device.

Although the present invention has been described with reference to various embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

We claim:

1. A device for non-invasive monitoring thermal stress of a user comprising:
   a. a monitoring unit comprising
      1) a first substrate comprising a first side and an opposite second side; and
      2) at least two temperature sensors, wherein at least one temperature sensor is located of the first side of the first substrate and at least one temperature sensor is located on the second side of the first substrate, each temperature sensor is directly or indirectly connected to said first substrate;
   b. a cover comprising a first side and an opposite second side, where the first side of said cover has a defined surface area, said defined surface area has a first area and a second area, said cover being adapted to receive the monitoring unit in the first area of said defined area: and
   c. a thermally conductive member contacting the temperature sensor on the second side of the first substrate, the thermally conductive member extending through the second side of the cover.

2. The device according to claim 1, further comprising an adhesive applied to a portion of the second area of the cover.

3. The device according to claim 1, wherein the first substrate comprises a circuit board.

4. The device according to claim 1, wherein the monitoring unit further comprises a shell directly or indirectly connected to said first substrate, said shell essentially covers the second side of said first substrate.

5. The device according to claim 1, further comprising an alert mechanism wherein the alert mechanism comprises an audible alarm, a visual alarm, a tactile alarm, an action to provide heating or cooling to the user, or a combination thereof.

6. The device according to claim 2, further comprising a processor attached to the first substrate, where the processor is configured to receive input from each temperature sensor and the processor is configured to determine a core temperature of a user of the device.

7. The device according to claim 6, wherein the processor is configured to compare the measured core temperature to a stored core temperature value and/or the processor is configured to determine a rate of change in core temperature to a stored threshold rate of change in core temperature range, and where the processor is configured to output an alert signal when the measured core temperature is outside the stored core temperature or value the determined rate of change in core temperature or the stored threshold rate of change in core temperature range.

8. The device according to claim 1, wherein the cover comprises a flexible material.

9. The device according to claim 2, wherein the adhesive is a pressure sensitive adhesive adapted to be applied to the skin of a user.

10. The device according to claim 9, wherein said adhesive is covered with a release sheet.

11. The device according to claim 1, wherein the cover is removable from the monitoring unit and the cover is disposable, while the monitoring unit is reusable.

12. A device for non-invasive monitoring thermal stress of a user having a monitoring unit comprising
 a first substrate comprising a first side and an opposite second side;
 at least two temperature sensors, wherein at least one temperature sensor is located of the first side of the first substrate and at least one temperature sensor is located on the second side of the first substrate, each temperature sensor is directly or indirectly connected to said first substrate;
 a shell directly or indirectly connected to said first substrate, said shell essentially covers the second side of said first substrate; and
 a thermally conductive member, said thermally conductive member contacting the temperature sensor on the second side of the first substrate and extends through the shell.

13. A device for non-invasive monitoring thermal stress of a user comprising:
 a) a monitoring unit comprising
  (1) a first substrate comprising a first side and an opposite second side; and
  (2) at least two temperature sensors;
  (3) a processor;
  (4) an alert mechanism; and
  (5) a power supply;
 wherein
  at least one temperature sensor is located of the first side of the first substrate and at least one temperature sensor is located on the second side of the first substrate, each temperature sensor is directly or indirectly connected to said first substrate and each temperature sensor is connected to the processor;
  the processor is configured to compare the measured core temperature to a stored core temperature value and/or the processor is configured to determine a rate of change in core temperature to a stored threshold rate of change in core temperature range, and where the processor is configured to output an alert signal when the measured core temperature is outside the stored core temperature or value the determined rate of change in core temperature or the stored threshold rate of change in core temperature range;
  the alert mechanism is connected to the processor and is configured to alarm the user when the processor outputs the alert signal; and
  the power supply being connected to the processor and the power supply is configured to provide power to the processor and alert mechanism;
 b) a cover comprising a first side and an opposite second side, where the first side of said cover has a defined surface area, said defined surface area has a first area and a second area, said cover being adapted to receive monitoring unit in the first area of said defined area:
 c) a thermally conductive member contacting the temperature sensor on the second side of the first substrate, the thermally conductive member extending through the second side of the cover.

14. The device according to claim 13, wherein the alert mechanism comprises an audible alarm, a visual alarm, a tactile alarm, an action to provide heating or cooling to the user, or a combination thereof.

15. The device according to claim 13, wherein the cover comprises a flexible material.

16. The device according to claim 13, wherein the cover is removable from the monitoring unit and the cover is disposable, while the monitoring unit is reusable.

17. The device according to claim 13, further comprising an adhesive applied to a portion of the second area of the cover.

18. A method of monitoring thermal stress in a user, said method comprising
 a. providing a monitoring unit comprising a first substrate having a first side and an opposite second side; at least two temperature sensors, wherein at least one temperature sensor is located of the first side of the first substrate and at least one temperature sensor is located on the second side of the first substrate, each temperature sensor is connected to said first substrate;
 b. providing a cover comprising a first side and an opposite second side, where the first side of said cover has a defined surface area, said defined surface area has a first area and a second area, said cover being adapted to receive the monitoring unit such that the monitoring unit directly or indirectly contacts the first area of said defined area and an adhesive applied to a portion of the second area of the cover;
 c. placing the monitoring unit into the cover in the first area to create a monitoring unit/cover combination;
 d. applying the monitoring unit/cover combination to the skin of a user, such that the adhesive on the cover and the at least one temperature sensor on the first side of the first substrate contacts the skin of the user.

19. The method of claim 18, wherein the monitoring unit/cover combination is applied to the skin of the user in the temporal artery region of the skin.

* * * * *